United States Patent

Czech

Patent Number: 4,845,212
Date of Patent: Jul. 4, 1989

[54] PROCESS FOR THE PREPARATION OF CHROMOGENIC CRYPTAHEMISPHERANDS

[75] Inventor: Bronislaw P. Czech, Peekskill, N.Y.

[73] Assignee: Technicon Instruments Corporation, Tarrytown, N.Y.

[21] Appl. No.: 232,976

[22] Filed: Aug. 17, 1988

Related U.S. Application Data

[63] Continuation-in-part of Ser. No. 38,680, Apr. 15, 1987, abandoned.

[51] Int. Cl.$^4$ ............................................. C07D 273/08
[52] U.S. Cl. .................................................. 540/469
[58] Field of Search ........................ 540/469; 546/469

[56] References Cited

PUBLICATIONS

Miyaura et al., "Synthetic Communications", vol. 11, No. 7, pp. 513–519 (1981).
March "Advanced Organic Chemistry" 3rd Edition, pp. 16–17 (1985).

Primary Examiner—Robert T. Bond
Attorney, Agent, or Firm—Jeffrey M. Greenman

[57] ABSTRACT

The invention relates to a process in which a variety of cryptahemispherands bearing a chromogenic group attached to the partially preorganized moiety may be synthesized. The procedure of the present invention allows preparation of preferred chromogenic cryptahemispherands of the general formula:

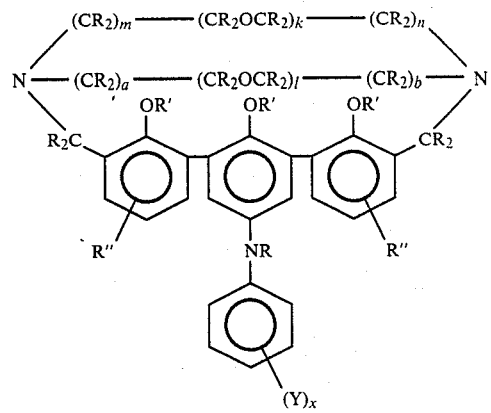

wherein:
R, is same or different, is hydrogen, lower alkyl, lower alkylidene, lower alkenyl, allyl, aryl, or benzyl;
R', same or different, is hydrogen, lower alkyl, lower alkylidene, lower alkenyl, allyl, aryl, or benzyl;
R", same or different, is hydrogen, lower alkyl, lower alkylidene, lower alkenyl, allyl, aryl, or benzyl;
Z is halogen;
Y is an electron withdrawing group, e.g., CN, $NO_2$, $CF_3$, COOR;
m is 1 to 3;
n is 1 to 3;
a is 1 to 3;
b is 1 to 3;
k is 1 to 3;
l is 1 to 3; and
x is 2 to 4.

2 Claims, 2 Drawing Sheets

PROCESS FOR THE PREPARATION OF CHROMOGENIC CRYPTAHEMISPHERANDS

CROSS-REFERENCE TO RELATED APPLICATION

This application is a continuation-in-part of Application Ser. No. 038,680, filed Apr. 15, 1987, entitled "Process for the Preparation of Chromogenic Cryptahemispherands", now abandoned.

BACKGROUND OF THE INVENTION

1. Field of the Invention

The present invention relates to a class of compounds generally known as chromogenic cryptahemispherands useful in the measurement of ions and more particularly, to a process for the preparation of such chromogenic cryptahemispherands.

2. Description of the Prior Art

Certain terms used in the present discussion should be defined to assure that the reader is of the same mind as the author as to their respective meanings. Thus the following definitions are provided to clarify the scope of the present invention.

The term "ionophore" includes, broadly, molecules capable of forming a complex with an ion in solution. For example, the cyclic polypeptide, valinomycin, binds selectively to potassium ions in solution to form a cationic complex. Also included in this term are podands, corands, cryptands, hemispherands, cryptahemispherands and spherands.

A "podand" is an organic linear compound containing donor or receptor atoms which has the capacity of associating with positively charged ions to form complexes.

The term "corands" refers to monocyclic compounds which contain electron donor atoms or acceptor atoms, which are electron rich or deficient, and which are capable of complexing with particular cations or anions because of their unique structures. Because of the unique sizes and geometries of particular corands, they are adaptable to complexing with various ions. In so complexing, the electron rich atoms, such as the oxygens in a corand, become spacially oriented towards the electron deficient cation. The carbon atom segments of the cycle are simultaneously projected in a direction outwards from the ion. Thus, the resultant complex is hydrophilic in the center, but is relatively hydrophobic at its perimeter.

"Cryptands" refers to polycyclic analogs of the corands. Accordingly, they include bicyclic and tricyclic multidentate compounds. In the cryptands, the cyclic arrangements of donor atoms is three dimensional in space, as opposed to the substantially planar configuration of the corands. A cryptand is capable of virtually enveloping the ion in three dimensional fashion and, hence, is capable of strong bonds to the ions in forming the complex. As with the corands, the donor atoms can include such atoms as oxygen, nitrogen and sulfur. The term "hemispherands" refers to macrocyclic or macropolycyclic ionophore systems, whose cavities are partially preorganized for binding by the rigidity of the hydrocarbon support structure and the spatial and orientational dictates of appended groups.

The designation "cryptahemispherand" was given by Donald J. Cram in 1986 (Cram, et al., *J. Am. Chem. Soc.*, 108 pp. 2998-3005 (1986)) to the class of macrobicyclic compounds which show an extraordinary propensity for complexation of alkali metal cations. Cryptahemispherands combine the partially preorganized cavity features of the hemispherands, but contain multiple other ligand-gathering features of the cryptands. The generic structure of a cryptahemispherand is depicted, infra, as structure (I).

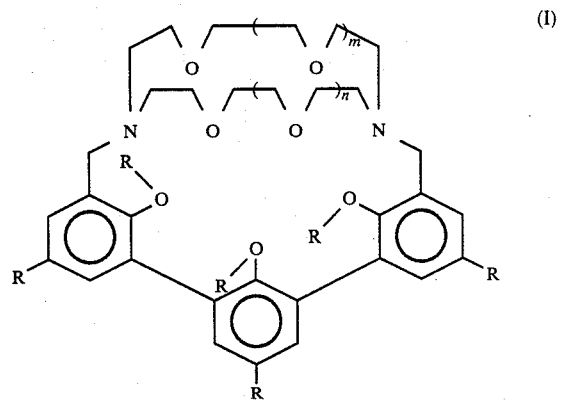

wherein:
R is hydrogen, alkyl, alkylidene, alkenyl, allyl, aryl or benzyle;
m is 0 to about 2; and
n is 0 to about 2;

Certain compounds were described in the literature prior to Cram, et al. supra, which are capable of not only behaving as ionophores by forming cation complexes, but also, when complexed, exhibit a detectable formation of or change in color.

Thus, experiments were published in 1977 whereby chromogenic moieties were covalently attached to ionophores to achieve a color change response to potassium (Takagi, et al., *Analytical Letters*, 10(3), pp. 1115-1122 (1977)). There it is taught to couple covalently a chromogenic moiety such as 4-picrylamino to an ionophore such as benzo-15-corand-5. Moreover, U.S. Pat. No. 4,367,072 mentions many corands, cryptands and podands covalently substituted with a chromogenic group, such as

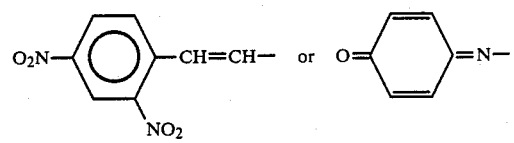

Yet another reference, German Offenlegungschift No. 3202779, published Aug. 4, 1983 discloses a chromogenic cryptand structure.

Although the synthesis of non-chromogenic cryptahemispherands have been described by Cram, et al., incorporation of a chromogenic moiety into the cryptahemispherand structure requires different synthetic strategy and has not been described before.

SUMMARY OF THE INVENTION

The invention relates to a process in which a variety of chromogenic cryptahemispherands of the general structure (I) may be synthesized in a direct fashion. The process is a nine-reaction preparation of cryptahemispherands bearing a chromogenic group attached to the partially preorganized moiety. The procedure of the present invention allows preparation of preferred chromogenic cryptahemispherands of the general formula:

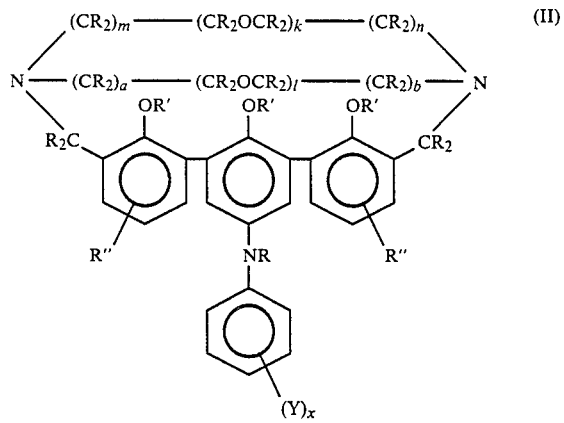

wherein:
R, same or different, is hydrogen, lower alkyl, lower alkylidene, lower alkenyl, allyl, aryl or benzyl;
R', same or different, is lower alkyl, lower alkylidene, lower alkenyl, allyl, aryl or benzyl;
R", same or different, is hydrogen, lower alkyl, lower alkylidene, lower alkenyl, allyl, aryl or benzyl;
Z is halogen;
Y is an electron withdrawing group, e.g., CN, $NO_2$, $CF_3$, COOR;
m is 1 to 3;
n is 1 to 3;
a is 1 to 3;
b is 1 to 3;
k is 1 to 3;
l is 1 to 3; and
x is 2 to 4.

The term "lower alkyl", as used in the present disclosure includes an alkyl moiety, substituted or unsubstituted, containing 1–4 carbon atoms. Included in the meaning of lower alkyl are methyl, ethyl, n-propyl, isopropyl, n-butyl and tert-butyl.

"Lower alkylidene" is used herein in the same context as "lower alkyl", but designates an alkylene group (i.e., a divalent alkyl) having 1–4 carbon atoms. The term lower alkylidene includes, but is not limited to, methylene, ethylidene, n-propylidene, iso-propylidene, n-butylidene, sec-butylidene and tert-butylidene.

The term "aryl" includes substituted or unsubstituted aryl moieties containing 6–12 carbon atoms, such as, for example, phenyl, tolyl, butyl phenyl, naphthyl ethyl, chlorophenyl, nitrophenyl and carboxyphenyl.

"Lower alkenyl" as used herein designates an lower alkenyl moiety, substituted or unsubstituted, having 1 to 4 carbon atoms and includes, for example, ethenyl, 1-propenyl, 2-propenyl, isopropenyl, 1-butenyl, 2-butenyl, 3-butenyl, isobutenyl, and tert-butenyl.

The above moieties may be unsubstituted or substituted as noted providing any such substituents do not interfere with the operation or functioning of the presently claimed invention.

BRIEF DESCRIPTION OF THE DRAWINGS

In the appended drawing, which is presented to further describe the invention, and to assist in its understanding through clarification of its various aspects, FIGS. 1A and 1B describe a reaction pathway for synthesizing preferred chromogenic cryptahemispherands of the general structure (II).

DETAILED DESCRIPTION OF THE INVENTION

Figure 1A:
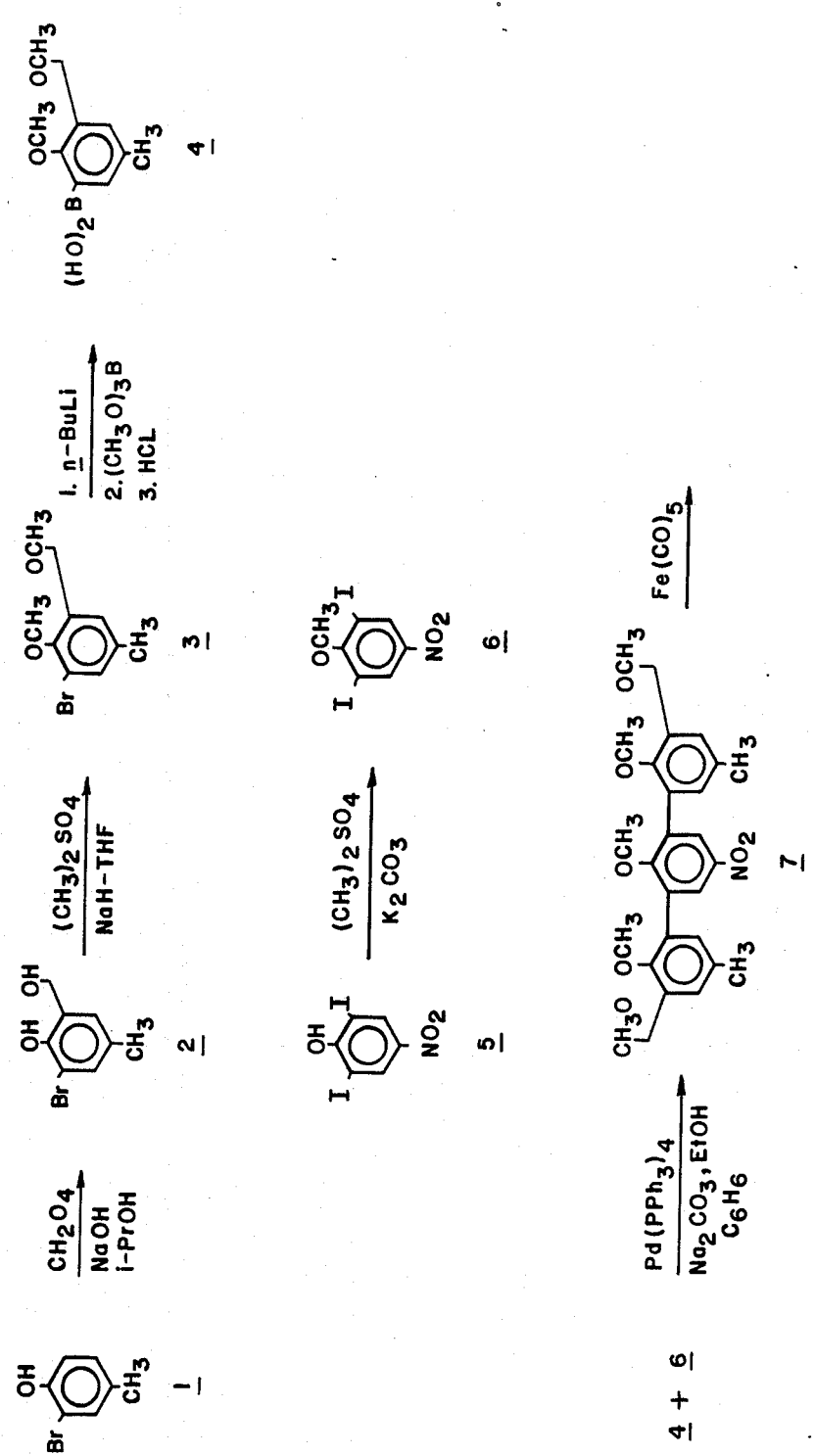

The chromogenic cryptahemispherand of the general structure (II) can be synthesized in accordance with the reaction pathway depicted in FIGS. 1A and 1B and described in detail below.

Preparation of Known Intermediate Compounds 2 and 6

The 2-bromo-6-(hydroxymethyl)-methylphenol 2 used in the following preparation was obtained from commercially available 2-bromo-4-methylphenol 1 by the method described in the article by Cram, et al., *J. Am. Chem. Soc.*, 106 pp. 4977–4987 (1984).

The 4-nitro-2,6-dimethylanisole 6 was prepared from commercially available 4-nitro-2,6-diiodophenol 5 by the method described in the article by Block, et al., *J. Am. Chem. Soc.*, 64 pp. 1070–1074 (1942).

Both of the articles are incorporated herein by reference.

Preparation of Compound 3

To a solution of 2 (23.4 g, 107.8 mmol) in 600 ml of THF under Ar at 0° C. was added 15.2 g (381 mmol) of 60% NaH. After warming to room temperature, 45.7 g (360 mmol) of dimethyl sulfate was added and the mixture was refluxed 18 h, cooled to 0° C. and methanol was added to decompose the excess NaH. The solvent was removed in vacuo to give a crude product which was dissolved in 100 ml of $CHCl_3$ and brine was added. The organic layer was separated, dried ($MgSO_4$) and evaporated. The residue was purified on a silica gel column (flash) with benzene-cyclohexane (1:4→1:1) to afford 23.7 g (90%) of 3 as a colorless liquid.

The $^1$H NMR spectrum ($CDCl_3$) gave absorptions at $\delta$2.29 (s, $ArCH_3$, 3H), 3.43 (s, $OCH_3$, 3H), 3.82 (s, $\overline{OCHHD}$ 3, 3H), 4.48 (s, $Ar\overline{CH_2}$, 2H), 7.14 (d, $Ar\underline{H}$, 1H) and 7.30 (d, $Ar\underline{H}$, 1H). Calcd. for $C_{10}H_{13}BrO_2$ (percent): C, 49.00; H, 5.35. Found (percent): C, 49.11; H, 5.34.

Preparation of Compound 4

To a solution of 3 (13.0 g, 53 mmol) in 200 ml of THF under Ar at −78° C. was added 22.5 ml of 2.4M n-BuLi (hexane). After stirring for 8 min, the lithiation solution was cannulated over 15 min into 48.0 g (460 mmol) of trimethyl borate in 125 ml of THF at −78° C. The mixture was stirred 30 min at −78° C. over 45 min, diluted with 400 ml of 2N HCl, and stirred 1 h at 25° C. Ether (250 ml) was added, the mixture was stirred 6 h at 25° C., and the layers were separated. The aqueous layer was extracted with fresh ether (3×100 ml). The combined ether extracts were extracted with 3N aqueous NaOH (4×100 ml). The base extracts were cooled to 5° C. and acidified to pH1 with concentrated HCl. Extraction of the aqueous solution with ether (3×100 ml) gave after evaporation of the solvent (room temperature, vacuum) 10.5 g (95%) of a colorless viscous oil 4 which solidified during storage at −5° C. and was used without further purification.

The $^1$H NMR spectrum (($CD_3$)$_2$CO) gave absorptions at $\delta$2.29 (s, $ArCH_3$, 3H) 3.38 (s, OCH, 3H), 3.80 (s, $OCH_3$, 3H), 4.45 (s, $Ar\overline{CH_2}$, 2H), 7.29 (d, $\overline{ArH}$, 1H) and 7.52 (d, $Ar\underline{H}$, 1H).

Preparation of Compound 7

To a mixture of 6 (4.00 g, 9.9 mmol), and 4 (5.00 g, 24.0 mmol) in 60 ml of toluene and 15 ml of ethanol was added under Ar 30 ml of 2M aqueous $Na_2CO_3$. To this vigorously stirred two-phase mixture was added 0.60 g (0.52 mmol) of tetrakis (triphenylphosphine)palladium (0) and the mixture was refluxed for 45 h. The layers were separated and the organic layer was dried ($MgSO_4$), evaporated and the residue was column chromatographed on alumina with benzene, and benzene-ethyl acetate (20:1) to give 4.44 g (93%) of 7 as a very viscous, pale yellow oil.

The mass spectrum (70 eV) gave the expected molecular ion at m/e 481. The $^1H$ NMR spectrum ($CDCl_3$) gave absorptions at $\delta2.36$ (s, $ArCH_3$, 6H), 3.30 (s, $OCH_3$, 3H), 3.47 (s, $OCH_3$, 6H), 3.49 (s, $OCH_3$, 6H), 4.54 (s, $ArCH_2$, 4H), 7.12 (d, $ArH$, 2H), 7.28 (d, $ArH$, 2H) and 8.25 (s, $ArH$, 2H).

Calcd. for $C_{27}H_{31}NO_7$ (percent): C, 67.35, H, 6.49. Found (percent): C, 67.27; H, 6.38.

Preparation of Compound 8

To a mixture of 7 (4.65 g, 9.7 mmol) in 175 ml of benzene and 175 ml of 1N NaOH under Ar was added 4.65 g (23.7 mmol) of iron pentacarbonyl. The mixture was stirred for 18 h at room temperature, 500 ml of benzene was added, and the benzene layer was separated. The aqueous layer was extracted with benzene (2×100 ml), the combined organic layers were filtered through Celite (twice), dried ($K_2CO_3$), filtered and evaporated to a 70 ml volume and a residue was column chromatographed on silica gel (flash) with petroleum ether-ethyl acetate (3:1→1:1) to give 2.88 g (66%) of 8 as a heavy, pale yellow oil which solidified during storage.

The mass spectrum (70 eV) gave the expected molecular ion at m/e 451. The $^1H$ NMR spectrum ($CDCl_3$) gave absorptions at $\delta2.33$ (s, $ArCH_3$, 6H), 3.14 (s, $OCH_3$, 3H), 3.45 (s, $OCH_3$, 6H), 3.51 (s, $OCH_3$, 6H), 4.54 (s, $ArCH_2$, 4H), 6.70 (s, $ArH$, 2H), 7.13 (s, $ArH$, 2H) and 7.19 (s, $ArH$, 2H).

Calcd. for $C_{27}H_{33}NO_6$ (percent): C, 71.82; H, 7.37. Found (percent): C, 71.75; H, 7.56.

Preparation of Compound 9

A mixture of 8 (2.75 g, 6.1 mmol), picryl chloride (2.00 g, 8.1 mmol) and $NaHCO_3$ (0.51 g, 6.1 mmol) in 325 ml of methanol under Ar at room temperature was stirred overnight, the solvent was removed in vacuo (room temp.) and a residue was dissolved in $CHCl_3$—$H_2O$ (110 ml of each). The chloroform layer was dried ($MgSO_4$), concentrated to 10 ml and column chromatographed on silica gel (flash) with petroleum ether-ethyl acetate (2:1) to give 3.82 g (95%) of 9 as a red foam.

The mass spectrum (70 eV) gave the expected molecular ion at m/e 662. The $^1H$ NMR spectrum ($CDCl_3$) gave absorptions at $\delta2.35$ (s, $ArCH_3$, 6H), 3.23 (s, $OCH_3$, 3H), 3.46 (s, $OCH_3$, 6H), 3.53 (s, $OCH_3$, 6 H), 4.53 (s, $ArCH_2$, 4H), 7.09–7.25 (m, $ArH$, 6H), 9.08 (s, $ArH$, 2H) and 10.29 (s, NH, 1H).

Calcd. for $C_{33}H_{34}N_4O_{11}$ (percent): C, 59.81; H, 5.17. Found (percent): C, 59.86; H, 5.36.

Preparation of Compound 10

Anhydrous HBr was bubbled into a solution of 9 (2.05 g, 3.1 mmol) in 650 ml of $CHCl_3$ for 10 min. After stirring an additional 10 min in the solution was poured into 800 ml of water and the mixture was stirred over 30 min. The organic layer was dried ($MgSO_4$), concentrated to 10 ml and column chromatographed on silica gel with $CH_2Cl_2$ to afford 1.79 g (75%) of 10 as a red glass.

The $^1H$ NMR spectrum ($CDCl_3$) gave absorptions at $\delta2.34$ (s, $ArCH_3$, 6H), 3.23 (s, $OCH_3$, 3H), 3.62 (s, $OCH_3$, 6H), 4.61 (s, $ArCH_2$, 4H), 7.09–7.24 (m, $ArH$, 6H), 9.09 (s, $ArH$, 2H) and 10.30 (NH, 1H).

Calcd. for $C_{31}H_{28}Br_2N_4O_9$ (percent): C, 48.07; H, 3.71. Found: C, 48.70; H, 3.71.

Cryptahemispherand 11

To a vigorously stirred solution containing 0.49 g (6.6 mmol) of anhydrous $Li_2CO_3$ in 100 ml of $CH_3CN$ was added over a period of 20 h 1,7-dioxa-4,10-diazacyclododecane (0.022 g, 1.25 mmol) in $CH_3CN$ (27 ml) and dibromide 10 (0.95 g, 1.25 mmol) in 27 ml of $CH_3CN$ at reflux. After addition was completed, reflux was continued for additional 15 h, then the solvent was removed in vacuo (25° C.) and the residue was chromatographed on a silica gel column with $CH_2Cl_2$—$CH_3OH$ (95:5) to afford 0.54 g (56%) of an orange foam which is a complex of 11 with lithium bromide.

The $^1H$ NMR spectrum ($CDCl_3$) showed absorptions at $\delta2.36$ (s, $ArCH_3$, 6H), 2.53 (s, $OCH_3$, 3H), 2.36–2.72 (m, $NCH_2$, 8 H), 3.12–4.19 (m, $OCH_2$, $NCH_2$, $OCH_3$, 18H), 7.05 (d, $ArH$, 2H), 7.14 (d, $ArH$, 2H), 7.28 (s, $ArH$, 2H) and 9.09 (s, $ArH$, 2H).

Figure 1B:
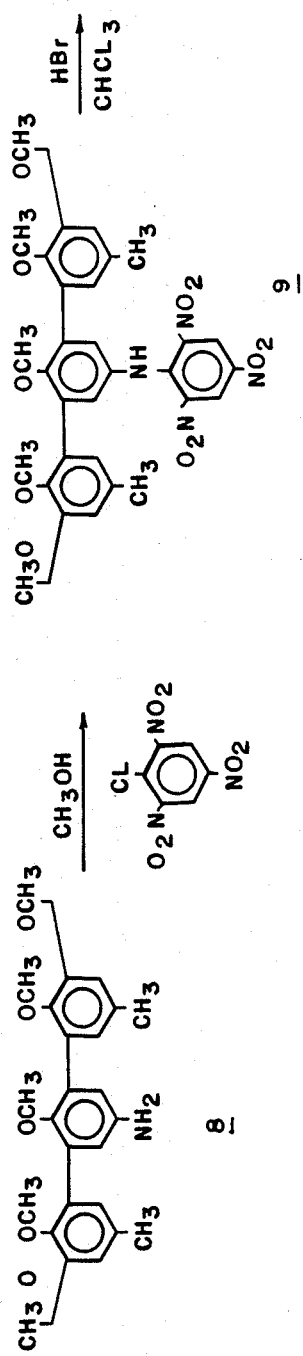
Figure 1B:
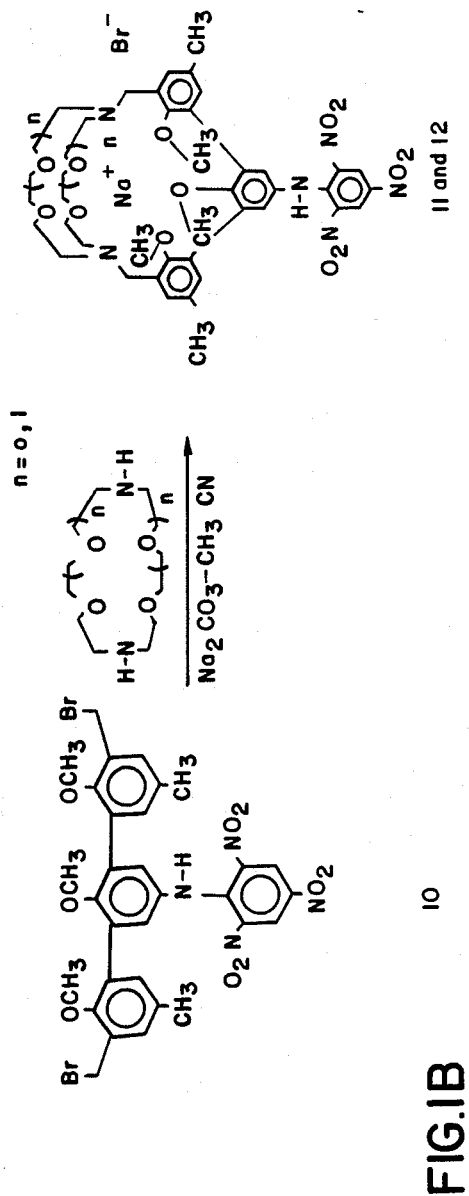

The cryptahemispherand 11 has the structure shown in FIG. 1 wherein n is 0.

Cryptahemispherand 12

To a vigorously stirred solution containing 0.85 g (8.0 mmol) of anhydrous $Na_2CO_3$ in 120 ml of $CH_3CN$ was added over a period of 20 h Kryptofix ®22 (0.42 g, 1.6 mmol) in $CH_3CN$ (35 ml) and dibromide 10 (1.22 g, 1.6 mmol) in $CH_3CN$ (35 ml) at reflux. After addition was completed, reflux was continued for additional 15 h, then the solvent was removed in vacuo (25° C.) and the residue was chromatographed on a silica gel column with $CH_2Cl_2$—$CH_3OH$ (95:5→90:10) to give 1.30 g (84%) of 12 as a dark red powder. The product is a complex of 12 with NaBr.

The $^1H$ NMR spectrum ($CDCl_3$) showed absorptions at $\delta2.36$ (s, $ArCH_3$, 6H), 2.84 (s, $OCH_3$, 3H), 3.48 (s, $OCH_3$, 6H), 2.18–4.10 (m, $NCH_2$, $OCH_2$, 24H), 2.67 (d, $ArCH_2N$, 2H), 4.20 (d, $ArCH_2N$, 2H), 7.03 (d, $ArH$, 2H), 7.12 (d, $ArH$, 2H), 7.17 (s, $ArH$, 2H) and 9.09 (s, $ArH$, 2H).

The cryptahemispherand 12 has the structure shown in FIG. 1B wherein n is 1.

The invention has been particularly described with reference to the preparation of compounds 11 and 12. It is to be understood that all the other compounds falling within formula II as defined herein, can be made in essentially the same way by choosing the appropriate reactant(s) at each state of the process.

It should be understood by those skilled in the art that various modifications may be made in the present invention without departing from the spirit and scope thereof as described in the specification and defined in the amended claims.

What is claimed:

1. A process for the preparation of a chromogenic cryptahemispherand (I) having the formula

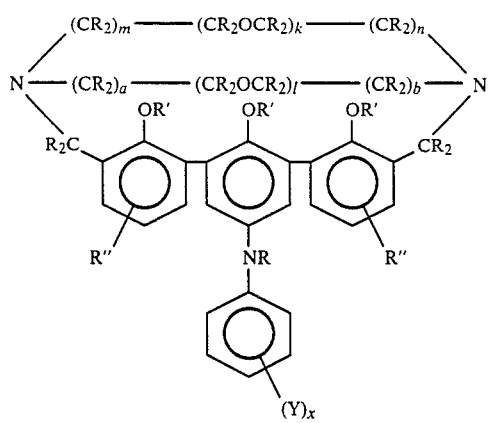 (I)

said process comprising the steps of:
(a) providing a compound (II) having the formula

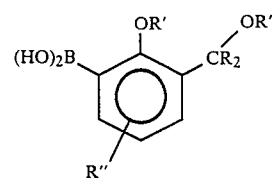 (II)

(b) providing a compound (III) having the formula

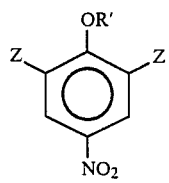 (III)

(c) reacting the compounds (II) and (III) in the presence of a catalyst to form a compound (IV) having the formula

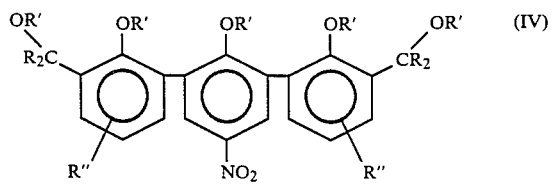 (IV)

(d) reducing the compound (IV) to form a compound (V) having the formula

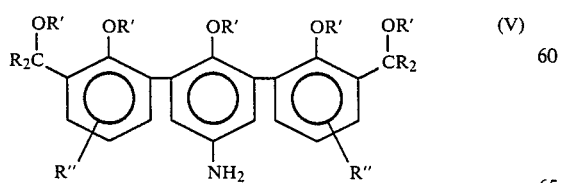 (V)

(e) reacting the compound (V) with a compound having the formula

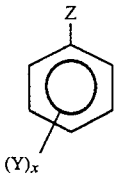

to form a compound (VI) having the formula

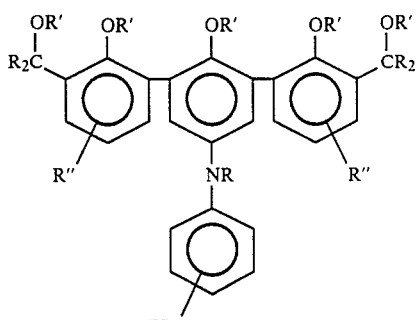

(f) halogenating the compound (VI) to form a compound (VII) having the formula

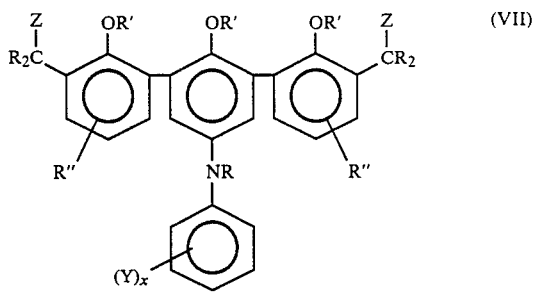 (VII)

(g) forming the chromogenic cryptahemispherand (I) by coupling the compound (VII) with a diazacorand having the formula

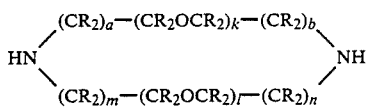

wherein:
R, same or different, is hydrogen, lower alkyl, lower alkylidene, lower alkenyl, allyl, aryl or benzyl;
R', same or different, is lower alkyl, lower alkylidene, lower alkenyl, allyl, aryl or benzyl;
R", same or different, is hydrogen, lower alkyl, lower alkylidene, lower alkenyl, aryl or benzyl;
Y is an electron withdrawing group;
Z is halogen;
a is 1 to 3;
b is 1 to 3;
k is 1 to 3;
l is 1 to 3;
m is 1 to 3;
n is 1 to 3; and
x is 2 to 4.

2. The method of claim 1 in which said catalyst of coupling step (c) is tetrakis(triphenylphosphine)palladium.

* * * * *